United States Patent [19]

Wilkinson-Tough

[11] Patent Number: 4,464,339
[45] Date of Patent: Aug. 7, 1984

[54] GAS SENSOR ELEMENTS AND METHODS OF MANUFACTURING THEM

[75] Inventor: Gordon S. Wilkinson-Tough, Gledhow, England

[73] Assignee: International Gas Detectors Limited, England

[21] Appl. No.: 516,095

[22] Filed: Jul. 22, 1983

Related U.S. Application Data

[62] Division of Ser. No. 221,272, Dec. 30, 1980, Pat. No. 4,416,911.

[30] Foreign Application Priority Data

Jan. 2, 1980 [GB] United Kingdom ................ 8000040

[51] Int. Cl.³ .......................................... G01N 27/16
[52] U.S. Cl. ........................................ 422/94; 338/34; 422/97; 427/125; 427/126.4
[58] Field of Search ........................ 73/27 R; 338/34; 340/633–634; 422/94–98; 436/151; 427/125, 126.4

[56] References Cited

U.S. PATENT DOCUMENTS

| 4,068,021 | 1/1978 | Allman | 422/83 |
| 4,132,673 | 1/1979 | Yamaguchi | 502/333 |
| 4,303,612 | 12/1981 | Sonley | 422/94 |
| 4,402,996 | 9/1983 | Gauger et al. | 427/125 X |

Primary Examiner—Michael S. Marcus
Assistant Examiner—Michael S. Gzybowski
Attorney, Agent, or Firm—Arnold, White & Durkee

[57] ABSTRACT

A gas sensor element for detecting the presence of a flammable gas comprises an electrical resistance filament surrounded by a bead which is formed by an array of alumina particles interspersed between and bound together only by particles of a catalyst to form an open porous gas diffusive skeletal matrix having a mean particle size of less than 20 nm. When the bead includes such a matrix, the number of active sites at which catalytic oxidation of flammable gases can take place is greatly increased with the result that the sensor element is very resistant to poisoning by atmospheric contaminants such as traces of silicone and sulphur compounds. The sensor thus has a very much longer life and does not require such frequent recalibration.

5 Claims, 7 Drawing Figures

GAS SENSOR ELEMENTS AND METHODS OF MANUFACTURING THEM

This is a divisional of application Ser. No. 221,272, filed Dec. 30, 1980 now U.S. Pat. No. 4,416,911, issued Nov. 22, 1983.

This invention relates to a gas sensing element for sensing the presence of a flammable gas and its method of manufacture and it is particularly concerned with the type of gas sensing element known as a pellistor.

Such gas sensing elements have been widely used and their basic construction is described in British Patent Specification No. 892,530. The elements are formed by a helically coiled filament embedded within a bead of refractory material such as alumina and the outer surface of the bead is coated with a layer of a catalyst. In use, an electrical heating current is passed through the coil of such a sensor and then if the sensor is exposed to air including some flammable gas, catalytic oxidation of the flammable gas takes place adjacent the surface of the bead which results in an increase in its temperature and results in the electrical resistance of the filament increasing. This change in electrical resistance is monitored by a resistance bridge circuit to give an electrical indication of the presence and concentration of a flammable gas.

Such a sensor is usually made by supporting the filament vertically and dipping it into an aqueous solution of a precursor of alumina, such as aluminium nitrate or hydroxide, and then this compound is converted into alumina by the passage of an electrical heating current through the filament. The dipping process is usually repeated to build up a bead of the required size around the filament. A solution or dispersion of the catalyst is then applied to the outer surface of the bead.

Whilst such sensors have been widely used, they have a poor resistance to poisoning and since the environment in which a flammable gas sensor is used frequently contains materials which poison the catalyst this means that the calibration of the sensor has to be checked frequently as a gradual increase in the level of poisoning of the catalyst leads to a gradual decrease in its sensitivity, and means that the sensor has to be replaced frequently.

British patent specification No. 1 387 412 in the name of English Electric Valve Company Limited describes and claims a gas sensor element formed by a helical coil consisting of a homogeneous mixture of an oxidation catalyst material and a substantially non-catalytic carrier material. This specification attributes the tendency of the gas sensor element to change in its electrical characteristics over a prolonged period to the diffusion of the catalyst into the carrier material. It suggests that this problem is overcome by having a homogeneous mixture of catalyst and carrier material. The specification only describes the bead as being made by a thermal decomposition process from a mixture of catalyst precursors and aluminium salts. It particularly discusses the bead as being formed from a solution of palladium chloride, platinum chloride, concentrated hydrochloric acid, distilled water and aluminium nitrate solution.

Another, more recent, patent specification, No. 1 556 339, in the name of English Electric Valve Company Limited acknowledges that changes in the electrical characteristics of gas sensing elements take place as a result of poisoning of the catalyst and suggests the incorporation of a zeolite into the bead to act as a molecular filter and absorb the catalyst poisons and thereby prevent them poisoning the catalyst.

Recently published European Patent Application No 0004184 also discusses the poisoning of the catalyst in a gas sensor element and discusses the preparation of the bead of the gas sensor element at least partly by deposition of a slurry formed of finely ground alumina having a particle size of less than 100 Å together with an aqueous binder. This bead is subsequently impregnated with a catalyst solution. The specification also discloses that the bead may include an initial coating of aluminium nitrate which is subsequently decomposed by a pulsed electrical current and the specification describes this decomposition by a pulsed electric current as resulting in an increase in the volume of the bead and suggests that it is this treatment of the bead which contributes greatly to the resistance to poisoning of the completed gas sensor element.

According to a first aspect of this invention, a gas sensor element comprises an electrical resistance filament surrounded by a bead which includes an array of alumina particles interspersed between and bound together only by particles of a catalyst for inducing catalytic oxidation of flammable gases to form an open porous gas diffusive skeletal matrix having a mean particle size of less than 20 nm.

According to another aspect of this invention, a method of making a gas sensor element comprises depositing on an electrical resistance filament a slurry formed by a mixture of alumina and at least one catalyst precursor in a substantially non-aqueous organic liquid, the mean particle size in the slurry being less than 20 nm, removing the liquid and decomposing the at least one catalyst precursor so that the filament is surrounded by a bead which includes an array of alumina interspersed between and bound together only by particles of a catalyst for inducing catalytic oxidation of flammable gases to form an open porous gas diffusive skeletal matrix having a mean particle size of less than 20 nm.

Preferably, the mean particle size of the catalyst precursors in the slurry and the mean particle size of the catalyst in the matrix is as small as possible and it is preferred that the mean particle size is below 5 nm. It is particularly important that the catalyst is in as finely divided a state as possible in the completed gas sensor and a preferred way of achieving and ensuring this is to subject the slurry formed by the mixture of alumina and at least one catalyst precursor in a substantially non-aqueous organic liquid to a wet grinding stage before depositing it on the electrical resistance filament. Alumina is a very abrasive material and when the slurry is subjected to a wet grinding stage the alumina grinds the at least one catalyst precursor and reduces its particle size.

It is important to obtain the alumina in as finely a divided state as possible but there is a limit imposed to the degree of fineness which is obtained when alumina is subjected to a simple grinding or milling operation as the individual particles of alumina agglomerate together to form larger units and these larger units of apparently greater particle size prevent the alumina being ground more finely. A particularly preferred way of obtaining at least some alumina of a sufficiently small particle size is to subject the alumina to a pre-treatment in which the alumina is mixed into a slurry with a substantially non-aqueous organic liquid and subjected to ultrasonic vibrations followed by a sedimentation step, with only the upper fraction so obtained then being mixed with the at least one catalyst precursor. This treatment with ultrasonic vibrations appears to break up at least some of the agglomerations of fine alumina particles and the sedimentation stage provides an effective size grading.

Preferably, the substantially non-aqueous organic liquid is a volatile liquid such as an alcohol, an ester, a ketone, a chlorinated aliphatic hydrocarbon, or an aliphatic hydrocarbon, for example petroleum ether. It is preferred to have the substantially non-aqueous organic liquid formed by methanol or ethanol. The catalyst is typically one of the noble metals such as platinum, palladium, or their salts and preferably, the catalyst is formed by a mixture of palladium and thorium. It has been found that a particularly good sensing element is obtained when the slurry is formed from a mixture of equal parts by weight of alumina, ammonium chloropalladite, and thorium nitrate.

It has also been found that better results are obtained if the filament is not dipped but, instead is supported horizontally and then has the slurry deposited onto it from, for example, a pipette. Shrinkage occurs during the manufacture which can lead to damage of the filament or the matrix when it is supported horizontally and so it is preferred that lead wires leading to the filament include kinks and are annealed so that the kinked portion can straighten to accommodate shrinkage of the matrix during removal of the liquid and subsequent decomposition of the catalyst precursors. After the slurry has been deposited on the filament an electric current is passed through the filament to drive off the liquid and decompose the catalyst precursors.

The bead may be built up by applying more than one layer of material to the filament. One type of standard pellistor has a bead substantially 2 mm in diameter and when a sensor in accordance with the present invention is required to have characteristics similar to this, conventional pellistor it is preferred that the matrix is built up in more than one layer and, typically, built up in three separate layers until the bead has a diameter of between 1.75 and 2.0 mm. Another type of conventional pellistor has a bead less than 1 mm in diameter and when a sensor element in accordance with this invention is required to have characteristics similar to this type of conventional pellistor the matrix can be built up with only a single application of slurry.

With a conventional sensor the catalyst, or the catalyst precursor, may be activated by heating the bead in air, or in the presence of a hydrocarbon gas. With a sensor of conventional construction, this heating step merely activates the catalyst. Alternatively with conventional sensors the catalyst may be activated by other means but, with a sensing element in accordance with this invention, it is especially preferred that the sensor is treated by exposing it to a stoichiometric mixture of a hydrocarbon gas and air whilst a current is passed through the filament, the current passing through the filament being the typical operating current of the sensing element in use. Catalytic oxidation of the hydrocarbon gas takes place and the bead glows brightly. We have discovered that when a sensor element in accordance with the invention is treated in this way, the sensor is considerably more robust and the matrix has a greater mechanical strength.

Preferably, the completed gas sensor element in accordance with this invention is subjected to a constant "soak" for a period of time, typically 96 hours.

Sensor elements in accordance with this invention are very resistant to poisoning by atmospheric impurities and we believe that this results from the very finely divided and dispersed state of the catalyst, together with the open porous gas diffusive skeletal nature of the matrix. These two factors mean that a sensor in accordance with this invention has a very much greater number of available sites at which catalytic oxidation of flammable gases can take place than any of the other various different types of gas sensor element which have been described previously. When a catalyst is applied to a conventional gas sensor element, simply by coating the outer surface of the bead or by impregnating the bead with a catalyst, there is a very much greater concentration of catalyst on the surface of the bead than throughout the remainder of the bead. This greater concentration at the surface is more accessible to any impurities in the atmosphere and so more likely to be poisoned but, perhaps more importantly, this greater concentration of catalyst at the surface of the bead means that the catalyst is far more likely to be sintered during its conditioning or during use and this sintering and joining together of particles of catalyst reduces the number of active catalytic sites that are available.

Another factor affecting the state of division of the catalyst particles is their nature of formation. When the catalyst is derived from a solution the particles of catalyst precursor that grow during removal of the solvent vary considerably and uncontrollably in size and they are typically very large in comparison with the particle sizes with which this invention is concerned. Also, when both the catalyst precursors and the alumina precursors are obtained from solution as in the case in the homogeneous matrix disclosed in U.K. patent specification No. 1,387,142 it is possible for at least some of the catalyst to be completely trapped inside crystals and platelets of alumina and so not be available as a site of catalytic activity.

With the sensor in accordance with this invention, the very fine particle size of the catalyst precursors ensures that, upon decomposition of the precursors, the catalyst is in a very finely divided state. Also, the fine particle size of at least some of the alumina particles and their intimate mixture with the finely divided particles of catalyst precursor and, catalyst ensure that the alumina particles are interspersed between adjacent finely divided particles of catalyst to prevent them becoming sintered together either during manufacture or use of the gas sensor element. When the slurry is subjected to a pre-treatment with ultrasonic vibrations not all of the agglomerations of small alumina particles are broken up with the result that some of these large agglomerations of alumina particles are distributed throughout the bead. This inhomogeneity in the nature of the bead does not affect the sensor elements adversely and it is believed that it may even contribute to the better results that are obtained by providing gas paths through which the inflammable gases may enter the bead more easily.

The catalyst acts as the sole binder to bind together the array of alumina particles and this results in a more open and porous matrix than with any of the previous sensors described above and thus the active catalytic sites distributed throughout the beads are readily accessible by flammable gas molecules diffusing through the bead. Equally, the flammable gas molecules can readily diffuse through any of the agglomerations of alumina particles since these also have an open porous nature and are even free of particles of catalyst and so are likely to be even more porous than the remainder of the matrix.

In the prior art devices, such as that described in European Patent Application No. 0004184, the alumina particles although small in size are firstly bound together by the aqueous binder which fills some of the interstices between the adjacent alumina particles and then the subsequent application of the solution of catalyst means that further of the interstices between the alumina particles are filled. This reduces the porosity of the matrix still further and so prevents ready diffusion of flammable gases into the bead.

The gas sensor element in accordance with this invention thus has a much greater number of active catalytic sites available at which catalytic oxidation of flammable gas can take place and consequently there are naturally a greater number that have to be poisoned before the device ceases to operate. More importantly with the greater availability of the catalytic sites at which catalytic oxidation can take place, it is believed that the rate controlling step in the oxidation of the flammable gas in the region of the bead is the rate of diffusion of a flammable gas through a flammable gas depletion layer surrounding the bead instead of the rate of oxidation of the gas. The rate of diffusion of the flammable gas through a flammable gas depletion layer surrounding the bead is substantially slower since it is a bulk transport mechanism, unlike the rate of oxidation and consequently, since there are so many sites available in the bead at which catalytic oxidation can take place, all the while that there is an excess of these sites, it is the rate of diffusion through the depletion layer around the bead which provides the mechanism limiting the heat generated by the catalytic oxidation of the flammable gas. Thus, if some of the catalytic sites are poisoned, provided that there is still an excess number of catalytic sites, there will be no change in the rate of oxidation of the flammable gas and hence no change in the increase in temperature of the bead for a particular concentration of flammable gas.

We have also found that sensors in accordance with this invention have a very much longer life than those manufactured by the conventional processes and this is principally due to their greater resistance to poisoning. However, sensors in accordance with this invention also have a high mechanical strength and toughness and consequently are also very resistant to mechanical damage.

One example of a sensor and a method of making it, in accordance with this invention, will now be described and its performance contrasted with that of conventional sensors with reference to the accompanying drawings; in which.

Figure 1:
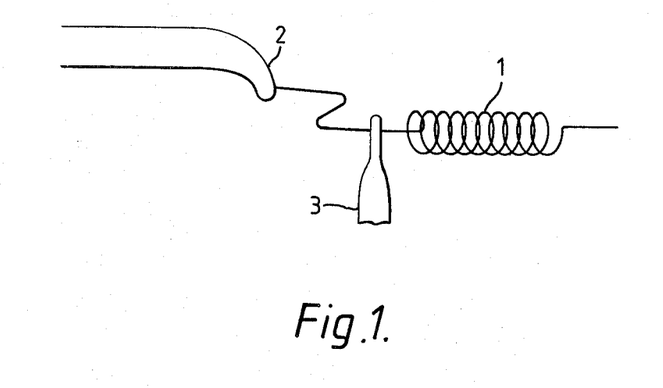
FIG. 1 is a perspective view illustrating the initial pre-treatment of the filament.
Figure 2:
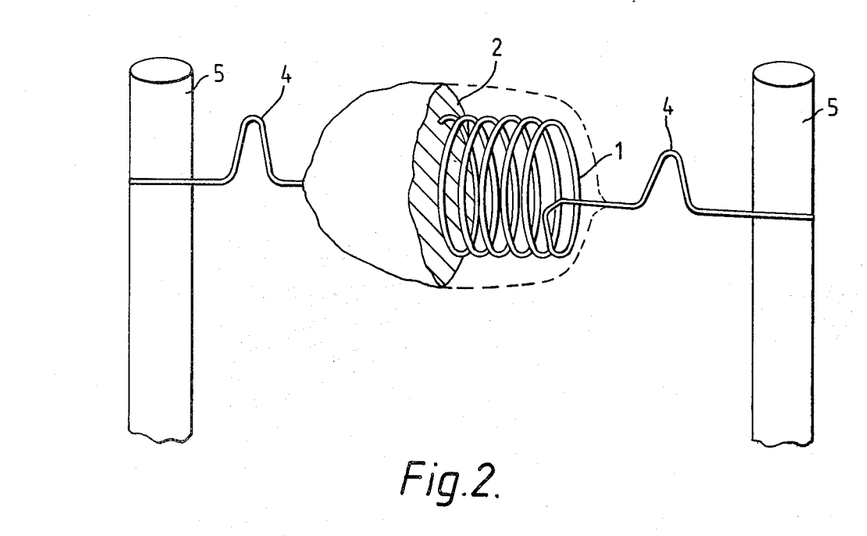
FIG. 2 is a partly cut-away perspective view of the complete sensor element.

A filament formed by a coil 1 is prepared by winding eleven turns of 0.05 mm hard drawn thermopure platinum wire having a resistance of 47 ohms per meter around a mandrel having a diameter of 0.5 mm against a tension of 15 grams. The coil 1 is then cleaned by immersion firstly in a solution of potassium permanganate in concentrated sulphuric acid, washed in tap water and then washed with a mixture of dilute nitric acid and hydrogen peroxide. The coil is then washed with de-ionised water and dried. One of the free ends of the wire leading to the coil is connected to a clip 2 and a pair of forceps 3 is used to hold the wire leading to the coil immediately adjacent the coil as shown in FIG. 1. The variable electric power supply is connected to the clip 2 and the forceps 3 and a current is passed along the lead wire between the clip 2 and the forceps 3 and the current is adjusted until the lead wire glows at a dull red heat. The wire leading to the coil is then bent into a kink 4 as shown in FIG. 1. The current to this portion of the lead wire is then reduced slowly to anneal this portion. A similar process is carried out on the opposite lead into the coil and then the lead wires of the coil are welded to a header including a pair of support posts 5 mounted in a standard can.

25 grams of alumina powder, gamma grade, having a mean particle size of less than or equal to 500 Å is mixed with 200 ml of methanol and agitated in an ultrasonic bath for 30 minutes. The mixture is then allowed to settle for 7 minutes and the supernatant slurry is decanted off the top of the sediment. The supernatant slurry is then left for 48 hours to settle. The methanol is decanted off the settled alumina and the alumina dried and stored. This dried alumina powder has a typical particle size of 200 nm or less. 1 gram of this dried alumina powder is mixed with one gram each of ammonium chlorpalladite and thorium nitrate. These three are placed in a grinding jar containing agate grinding elements and 7 ml of methanol. The compounds are mixed and ground together in a micronising mill for 15 minutes to provide a smooth slurry. The alumina particles or crystallites are very abrasive and, together with the agate grinding elements rapidly reduce the ammonium chloropalladite and thorium nitrate to crystallites having a typical particle size of 5 nm or less. The grinding step also ensures that complete and intimate mixing of the alumina, ammonium chloropalladite and thorium nitrate takes place.

The header is mounted in a jig so that the coil 1 is horizontal and with an electrical power supply connected between the support posts 5. A drop of slurry is placed on the platinum coil 1 using a small pipette and any excess slurry removed by lightly touching the base of the coil 1. The slurry adheres to the coil 1. The slurry on the coil is allowed to dry for 3 minutes in air and then a current of 200 mA is passed through the coil for 1 minute. The current through the coil is then increased to a current of 275 mA for two minutes. This drives off the methanol. A further drop of slurry is then added to the coil and a current of 200 mA passed through the coil for one minute. A current of 300 mA is then passed through the coil for 2 minutes followed by a current of 360 mA for one minute. Further drops of slurry are placed on the coil with this three stage heating regime following each addition until a bead of material around the coil having a diameter of between 1.75 and 2.0 mm is formed. After completion, a current of 400 mA is passed through the coil for fifteen minutes and during this stage the ammonium chloropalladite and thorium nitrate at least partly decompose.

The sensor is then conditioned by applying a current of 400 mA, a typical operating current, through the coil and allowing it to run in air for five minutes. A flow of methane and air in stoichiometric proportions with 13% methane is then introduced over the surface of the bead for five minutes. During this conditioning process the catalyst precursors complete their decomposition to provide a very finely divided catalyst formed by particles of palladium metal and thorium oxide which bind together the alumina particles or crystallites. The sensor glows bright red during this period and this is followed by a further five minute period with an air flow passing over the beads. This current is then continued at least overnight with the sensors in static air to provide a constant current "soak" for the sensors to enable their characteristics to stabilise. This constant current soak may last a number of days, typically four days.

Figure 3A:
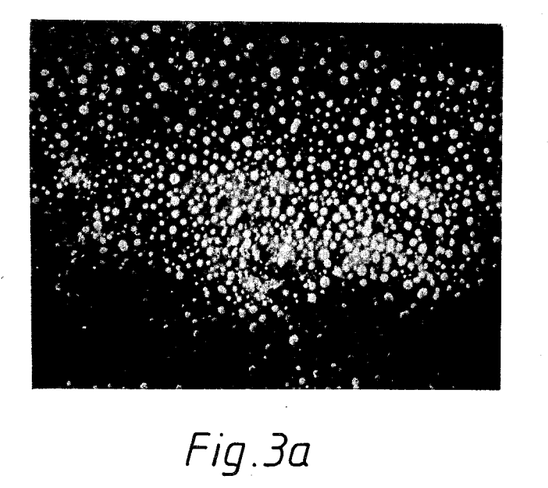
FIGS. 3a and 3b are photo-micrographs to the same scale of part of the matrix of a sensor in accordance with this invention and of a conventional sensor, respectively.
Figure 3B:
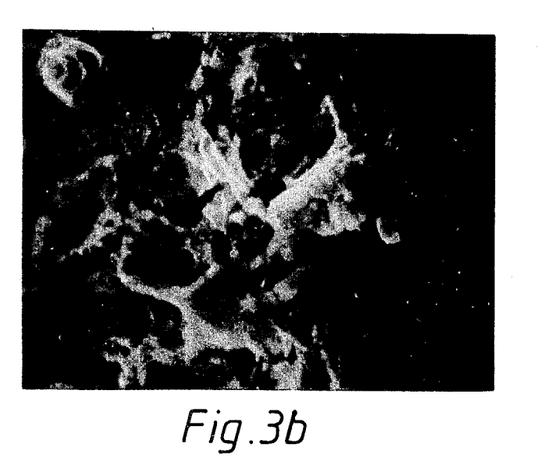

FIGS. 3a and 3b are photomicrographs of the bead produced using an electron microscope and it is clear from these Figures that there is a striking contrast between the bead of the device in accordance with this invention and that of a conventional device. The bead of the conventional device was formed from a solution of an alumina precursor and the photographs show the typical structure of such devices, which is that they are formed by large fractured platelets of alumina which typically have a size of 8000 nm, together with some sintered lumps of catalyst. The platelets themselves are substantially impermeable to inflammable gases. In contrast to this the example of the sensor in accordance with this invention includes a number of white round regions, which are formed by agglomerations of alumina particles, which have a typical bulk mean size of 150 nm, and which are permeable to the inflammable gases. The agglomerations of alumina particles are surrounded by a porous open gas diffusive skeletal matrix consisting of finely divided catalyst and alumina. It is this porous open gas diffusive skeletal matrix formed by alumina particles interspersed between and bound together only by particles of the catalyst which provide the large number of active catalytic sites that are then available at which catalytic oxidation of the flammable gases can take place.

Figure 4:
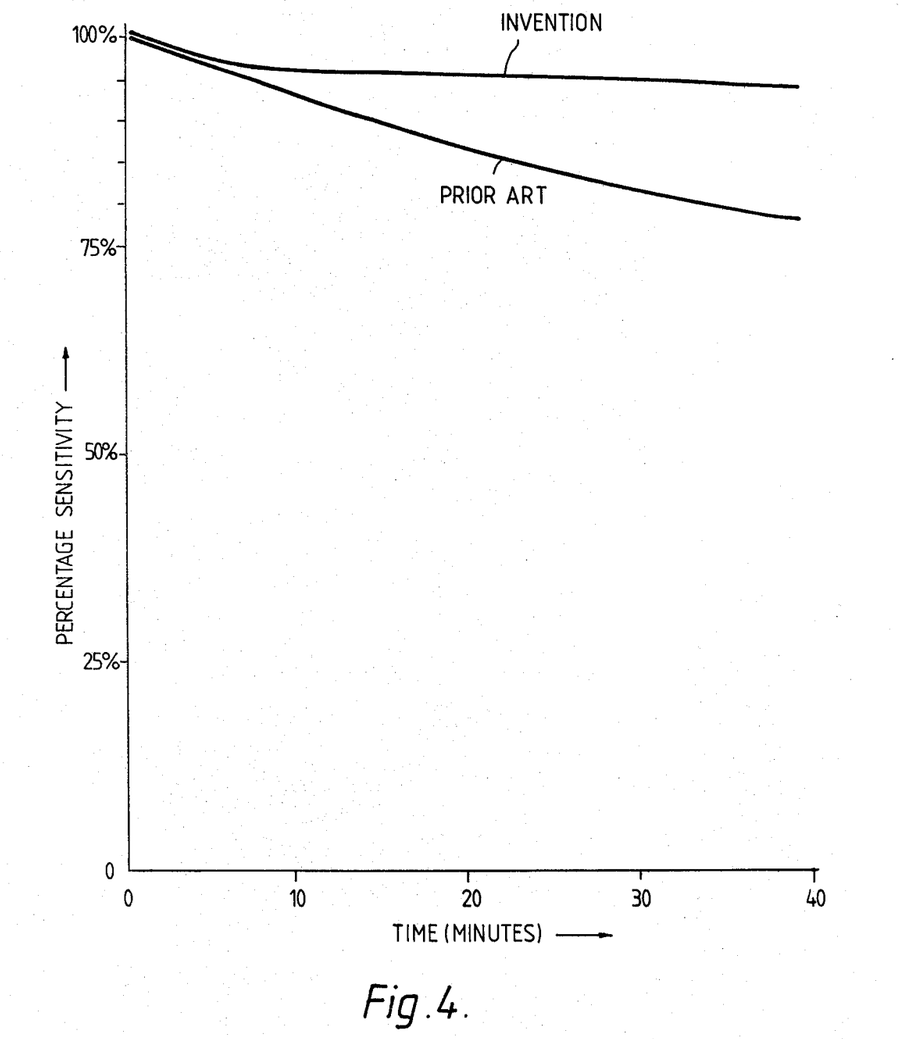
FIG. 4 is a graph of sensitivity against time contrasting the characteristics of a sensor in accordance with this invention with those of a conventional device.

FIG. 4 illustrates the results of a laboratory test in which a sensor made in accordance with this invention and a standard pellistor made by a method in accordance with the description of British Patent Specification No. 892 530 were exposed to a mixture of 50% L.E.L. (Lower Explosive Limit) petrol vapour in air. Lead compounds from the petrol vapour tends to poison the catalysts of both pellistors and the graph shown in FIG. 5 shows that they both start with similar initial declines in their sensitivity but then, the reduction in sensitivity of the sensor in accordance with this invention levels off whereas the sensitivity of the standard pellistor continued to decline.

Figure 5:
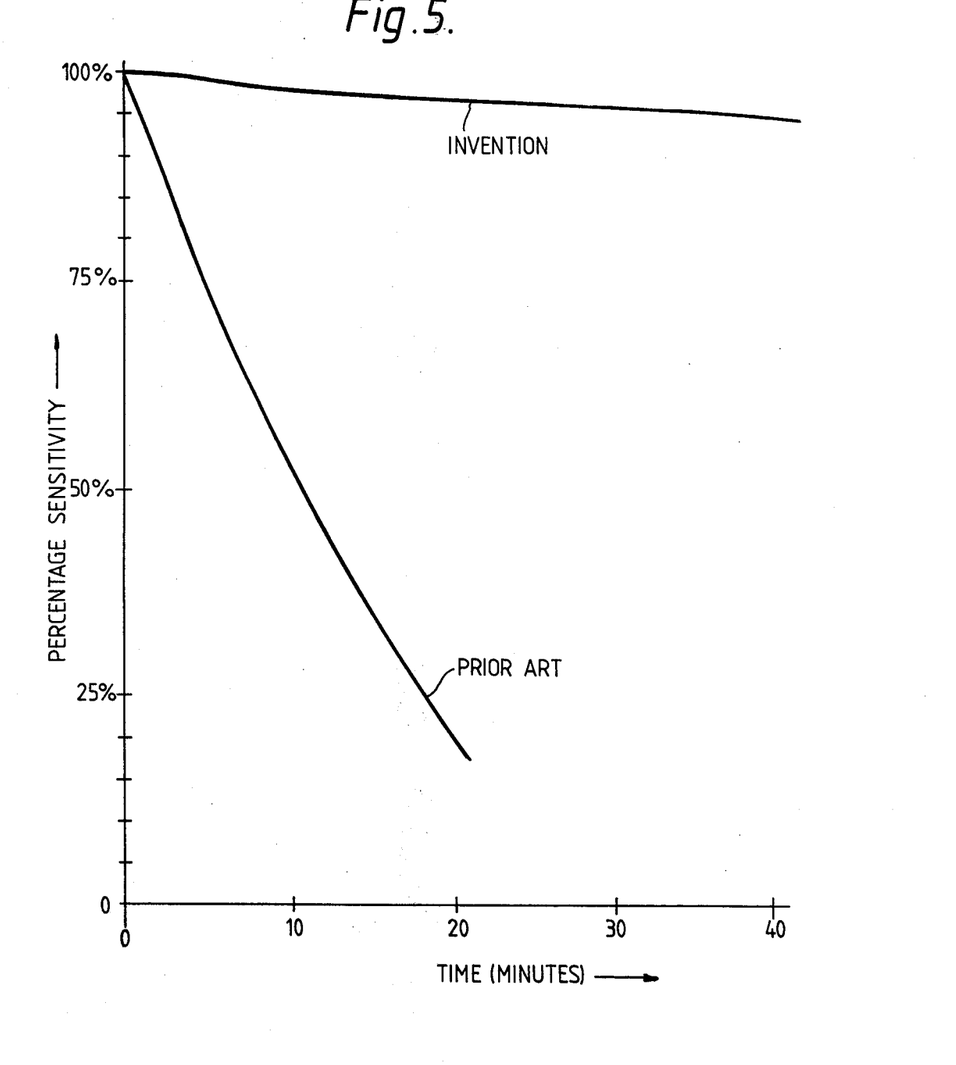
FIG. 5 is a graph of sensitivity against time contrasting the characteristics of a sensor in accordance with this invention with those of a conventional device; and, FIG. 6 is a graph showing the average loss in sensitivity against time for a group of sensors in accordance with this invention against a group of conventional sensors in a field trial.

FIG. 5 illustrates the results of another laboratory test again using a sensor in accordance with this invention and a standard pellistor in accordance with British specification No. 892 530. In this test, both pellistors were exposed to a concentration of 10 parts per million of hexamethyldisiloxane (HMDS) in air. The graph shows a marked difference in the rate of poisoning of the conventional pellistor and that in accordance with this invention.

Figure 6:
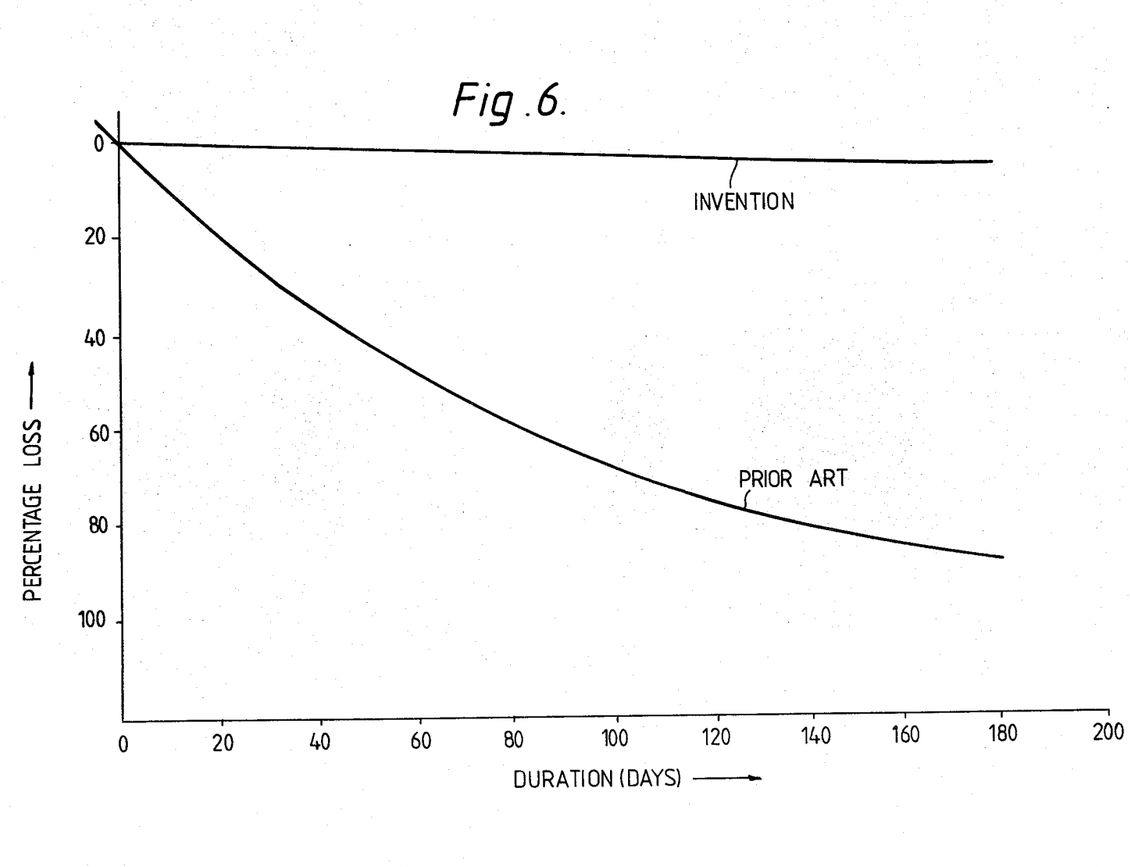

To confirm these laboratory test results, a field trial was carried out on an offshore platform in the Dunlin Alpha oilfield in the North Sea. The nature of the catalyst poison had not been defined but tests indicated that it was probably sulphur based. At each of ten locations around the platform both a sensor made in accordance with this invention and a standard pellistor made in accordance with British Patent Specification No 892 530 were installed. The sensors were all calibrated initially with a 0.95% butane/air mixture and then recalibrated at monthly intervals with the same gas/air mixture. Table I shows the result of the tests for the first six months with the sensors in accordance with this invention being marked with an asterisk. The average of these results is shown in the graph illustrated in FIG. 6. These show that the sensor in accordance with this invention is at least ten times more resistant to poisoning by the atmospheric impurities present in this location than the conventional sensor.

TABLE I

| Sensor Number | Initial Calibration (0.95% Butane) | RECALIBRATION FIGURE/ CUMULATIVE % CHANGE DATE | | | | |
|---|---|---|---|---|---|---|
| | | 16.4.80 | 20.5.80 | 9.7.80 | 6.8.80 | 11.9.80 |
| AS/10* | 60 | 67/+12 | 52/−13 | 60/−13 | 60/−13 | 59/−15 |
| I2/365 | 60 | 58/−3 | 30/−52 | 12/−90 | NO RESULT | |
| AS/16* | 65 | 58/−11 | 56/−15 | 58/−17 | 60/−20 | 60/−20 |
| I2/366 | 60 | 42/−30 | 20/−77 | 12/−95 | NO RESULT | |
| AS/8* | 63 | 65/+3 | 65/+3 | 63/0 | 60/−4 | 70/+6 |
| J2/256 | 60 | 50/−17 | 45/−38 | 20/−80 | 20/−93 | NO RESULT |
| AS/15* | 60 | 60/0 | 55/−8 | 60/−8 | 60/−8 | 60/−8 |
| J2/272 | 60 | 50/−17 | 50/−31 | 12/−86 | NO RESULT | |
| J2/16 | 60 | 9/−85 | 0/−100 | | NO RESULT | |
| AS/13* | 90 | 90/0 | 90/0 | 78/−13 | 90/0 | 85/−6 |
| I2/362 | 60 | 55/−8 | 60/−8 | 60/−8 | 62/−5 | 72/+13 |
| AS/18* | 60 | 75/+25 | 50/+4 | 57/−1 | 56/−7 | 65/0 |
| AS/11* | 60 | 60/0 | 68/+13 | 47/−11 | Water Damaged | No Result |
| I2/363 | 60 | 25/−58 | 15/−90 | | NO RESULT | |
| AS/12* | 80 | 73/−9 | 90/+12 | 80/0 | 70/−13 | 82/+2 |
| J2/252 | 60 | 55/−8 | 63/−4 | 30/−52 | 20/−84 | No Result |
| AS/9* | 60 | 58/−3 | No Result | 60/−3 | 60/−3 | 76/+22 |
| I2/367 | 60 | 30/−50 | 20/−83 | | NO RESULT | |
| J2/269 | 60 | No | 30/−50 | 25/−80 | 20/−93 | 25/−98 |

TABLE I-continued

| Sensor Number | Initial Calibration (0.95% Butane) | RECALIBRATION FIGURE/ CUMULATIVE % CHANGE DATE | | | | |
|---|---|---|---|---|---|---|
| | | 16.4.80 | 20.5.80 | 9.7.80 | 6.8.80 | 11.9.80 |
| | | Result | | | | |
| AS/14* | 60 | 56/−7 | 50/−22 | 70/−10 | 66/0 | 58/−3 |
| Average | DCP* | +1 | −2 | −7 | −7 | −2 |
| % Loss of Sensitivity | Standard Pellistor | −30 | −53 | −76 | >−82 | >−82 |
| Duration of Appraisal (Days) | 15.3.80 | 32 | 66 | 116 | 144 | 180 |

I claim:

1. A gas sensor element comprising an electrical resistance filament; and a bead surrounding said electrical resistance filament; said bead including alumina particles and particles of a catalyst for inducing catalytic oxidation of flammable gases, said alumina particles being interspersed between and bound together only by said particles of catalyst to form an open porous gas diffusive skeletal matrix, said matrix having a mean particle size of less than 20 nm.

2. The gas sensor element of claim 1, wherein said particles of catalyst have a mean particle size of less than 5 nm.

3. A gas sensor element comprising an electrical resistance filament surrounded by a bead which is formed by an array of alumina particles interspersed between and bound together only by particles of a catalyst to form an open porous gas diffusive skeletal matrix the gas sensor element comprising an element made by the steps of:
   providing such an electrical resistance filament;
   preparing a slurry from a mixture of alumina and at least one catalyst precursor in a substantially non-aqueous organic liquid, the mean particle size in the slurry being less than 20 nm;
   depositing said slurry on said electrical resistance filament; and,
   removing said non-aqueous organic liquid and decomposing said at least one catalyst precursor to thereby form the filament surrounded by a bead which includes an array of said alumina particles interspersed between and bound together only by particles of a catalyst for inducing catalytic oxidation of flammable gases to form an open porous gas diffusive skeletal matrix having a mean particle size of less than 20 nm.

4. A gas sensor element comprising an electrical resistance filament surrounded by a bead which is formed by an array of alumina particles interspersed between and bound together only by particles of a catalyst to form an open porous gas diffusive skeletal matrix the gas sensor element comprising an element made by the steps of:
   providing an electrical resistance filament;
   forming an alumina by mixing alumina into a slurry with a substantially non-aqueous organic liquid, subjecting the slurry to ultrasonic vibrations, allowing the vibrated slurry to sediment, and separating the upper fraction of the slurry to provide the alumina;
   preparing a slurry from a mixture of said alumina and at least one catalyst precursor in a substantially non-aqueous organic liquid, the mean particle size in said slurry being less than 20 nm;
   depositing said slurry on said electrical resistance filament; and
   removing said non-aqueous organic liquid and decomposing said at least one catalyst precursor to thereby form the filament surrounded by a bead which includes an array of said alumina particles interspersed between and bound together only by particles of a catalyst for inducing catalytic oxidation of flammable gases to form an open porous gas diffusive skeletal matrix having a mean particle size of less than 20 nm.

5. A gas sensor element comprising an electrical resistance filament surrounded by a bead which is formed by an array of alumina particles interspersed between and bound together only by particles of a catalyst to form an open porous gas diffusive skeletal matrix made by the steps of:
   providing an electrical resistance filament;
   preparing a slurry by mixing alumina having a nominal particle size of 50 nm with a substantially non-aqueous organic liquid;
   subjecting said slurry to ultrasonic vibrations;
   allowing said slurry to sediment;
   separating the upper fraction of said slurry;
   mixing alumina from said upper fraction with at least one catalyst precursor and a substantially non-aqueous organic liquid;
   subjecting said slurry to a wet grinding stage to reduce the mean particle size in the slurry to less than 20 nm;
   depositing said slurry on said electrical resistance filament;
   removing said non-aqueous organic liquid; and,
   decomposing said at least one catalyst precursor whereby said filament is surrounded by a bead which includes an array of said alumina particles interspersed between and bound together only by particles of a catalyst for inducing catalytic oxidation of flammable gases to form an open porous gas diffusive skeletal matrix having a mean particle size of less than 20 nm.

* * * * *